(12) United States Patent
Merenkova

(10) Patent No.: US 6,762,018 B1
(45) Date of Patent: Jul. 13, 2004

(54) ANALYSIS OF NUCLEOTIDE POLYMORPHISMS AT A SITE

(75) Inventor: Irena N. Merenkova, Moscow (RU)

(73) Assignee: Tetragen SA, Moscow (RU)

( * ) Notice: Subject to any disclaimer, the term of this patent is extended or adjusted under 35 U.S.C. 154(b) by 0 days.

(21) Appl. No.: 09/471,703

(22) Filed: Dec. 23, 1999

(51) Int. Cl.[7] ........................... C12Q 1/68; C12P 19/34; C07H 21/04

(52) U.S. Cl. ..................... 435/6; 435/91.2; 536/24.33
(58) Field of Search .................. 435/6, 91.2; 536/23.1, 536/24.3, 24.33

(56) References Cited

U.S. PATENT DOCUMENTS

| | | | |
|---|---|---|---|
| 5,518,900 A | 5/1996 | Nikiforov et al. | 435/91.1 |
| 5,679,524 A | * 10/1997 | Nikiforov et al. | 435/6 |
| 5,741,676 A | * 4/1998 | Fuller | 435/91.1 |
| 7,563,164 | 6/1998 | Reynolds et al. | 435/6 |
| 5,811,239 A | 9/1998 | Frayne | 435/6 |
| 5,849,487 A | 12/1998 | Hase et al. | 435/6 |
| 5,849,542 A | 12/1998 | Reeve et al. | 435/9.1 |
| 5,885,775 A | 3/1999 | Haff et al. | 435/6 |
| 5,888,819 A | 3/1999 | Goelet et al. | 435/5 |
| 5,925,520 A | 7/1999 | Tully et al. | 435/6 |
| 6,004,744 A | 12/1999 | Goelet et al. | 435/5 |
| 6,013,431 A | 1/2000 | Söderlund et al. | 435/5 |

FOREIGN PATENT DOCUMENTS

| | | | |
|---|---|---|---|
| EP | 0648280 | * 4/1995 | 435/6 |
| EP | 0 648 280 B1 | 5/1999 | |
| WO | WO 91/13075 | 9/1991 | |
| WO | WO 06/30545 | 10/1996 | |
| WO | WO 98/59066 | 12/1998 | |

OTHER PUBLICATIONS

Krook et al; Human Molecular Genetics, vol. 1, pp 391–395, 1992.*
Gibson et al; Journal of Capillary Electrophoresis, vol. 5, Jan–Apr. 1998; pp 73–80.*
Hu, et al. "Primer Specific and Mispair Extension Analysis (PSMEA) as a Simple Approach to fast Genotyping", Nucleic Acid Research, 1998, vol. 26(21) 5013–5015.
Krook, et al. "Rapid and Simultaneous Detection of Multiple Mutations by pooled and Multiplex Single Nucleotide Primer extension: application to the Study of Insulin–Responsive Glucose Transporter and Insulin receptor Mutations in Non–Insulin–Dependent Diabetes", Human Molecular Genetics, vol. 1(6) 391–395.
Liu et al., Cancer Research 54: 4590–4594, 1994.
"hMSH2 Mutations in Hereditary Nonpolyposis Colorectal Cancer Kindreds[1] ".
Landegren et al. Genome Research: 769–776, 1998.
"Reading Bits of Genetic Information: Methods for Single–Nucleotide Polymorphism Analysis".

Coille et al., Biochemistry, vol. 37, 1998, pp. 12672–12680. "Functional Comparison of Two Human Monocyle Chemotactic Protein–2 Isoforms, Role of the Amino–Terminal Pyroglutamic Acid and Processing by CD26/Dipeptidyl Peptidase IV".
Genbank Accession No. U41213, Posted on Genbank Nov. 29, 1995.
"Structure of the human MSH2 locus and analysis of two Muir–Torre kindreds for msh2 mutations".
Ross et al., Analytical Chemistry, vol. 59, No. 20, Oct. 15, 1997, pp. 4197–4202 "Discrimination of Single–Nucleotide Polymorphisms in Human DNA Using Peptide Nucleic Acid Probes Detected by MALDI–TOF Mass Spectrometry".*
Marino et al., Electrophoresis, vol. 17, 1996, pp. 1499–1504 "Characterization of mitochondrial DNA using low–stringency single specific primer amplification analyzed by laser induced fluorescence —capillary electrophoresis".*
Nikiforov et al., Nucleic Acids Research, vol. 22, No. 20, 1994, pp. 4167–4175 "Genetic Bit Analysis: a solid phase method for typing single nucleotide polymorphisms".*
Hacker et al. Analytical biochemistry, Vo 272, 1999, pp. 156–164 "Mutation Detection by Denaturing DNA Chromatography Using Flourescently Labeled Polymerase Chain Reaction Products".*
Lee et al. Bio Techniques, vol. 27, No. 2, Aug. 1999, pp. 342–349 "Seven–Color , Homogenous Detection of Six PCR Products".*
Fei et al., Nucleic Acids Research, vol. 26, No. 11, 1998, pp. 2827–2828 "MALDI–TOF mass spectrometric typing of single nucleotide polymorphisms with mass–tagged ddNTPS".*
Haff et al.,Nucleic Acids Research, vol. 25, No. 16, 1997, pp. 3749–3750 "Multiplex genotyping of PCR products with Mass Tag–labeled primers".*
Ross et al., Nature Biotechnology, vol. 18 Dec. 1998, pp. 1347–1351 "High level multiplex gentoyping by MALDI–TOF mass spectrometry".*
Pastinen et al., Clinical Chemistry, vol. 42, No. 9, 1996, pp. 1391–1397 "Multiplex, fluorescent, solid–phase minisequencing for efficient screening of DNA sequence variation".*

(List continued on next page.)

Primary Examiner—Jehanne Souaya
(74) Attorney, Agent, or Firm—Carol L. Francis; Bozicevic, Field & Francis LLP

(57) ABSTRACT

The identity of the polymorphic nucleotide in a target sequence having at least two known variants can be easily and efficiently detected by hybridizing at least one primer upstream of the biallelic marker and performing extension reactions using the target DNA with the hybridized primer, where a first reaction is conducted in the absence of a deoxyribonucleoside triphosphate or ribonucleoside triphosphate complementary to the first known variant, and a second reaction is conducted in absence of a deoxyribonucleoside triphosphate or ribonucleoside triphosphate complementary to the second known variant. Determining the lengths of the primers and any extension products from both reactions will indicate which variant or variants are present in a DNA sample.

19 Claims, 5 Drawing Sheets

OTHER PUBLICATIONS

Giordano et al., *Genomics*, vol. 56, 1999, pp. 247–253 "Identification by Denaturing High–Performance Liquid Chromatography of Numerous Polymorphisms in a Candidate Region for Multiple Sclerosis Susceptibilty".*

Li et al., *Electrophresis*, vol. 20, 1999, pp. 1256–1265 "single nucleotide polymorphism determination using primer ectension and time–of–flight mass spectrometry".*

Hoogendoom et al., *Hum Benet*, vol. 104, 1999, pp. 89–93 "Genotyping singel nucleotide polymorphisms by primer extension and high performance liquid chromatography".*

Haff et al., *Genome Research*, vol. 7, 1997, pp. 378–388 "Single–Nucleotid Pollymorphism Identification Assays Using a Thermosable DNA Polymerase and Delayed Extraction MALDI–TOF Mass Spectrometry".*

Liu et al., *Nucleic Acids Research*, vol. 26, No. 8, 1998, p. 1396–1400 "Denaturing high performance liquid chromatography (DHPLC) used in the detection of gemline and somatic mutations".*

Bogaert et al., Am. J. Hum. Genet, vol. 55, 1994, pp. 1128–1136 "Expression, in Cartilage, of a 7–Amino–Acid Deletion in Type #Collage from Two Unrelated individuals with Kniest Dysplasis".*

Whitney et al., *Experimental Hematology*, vol. 22, 1994, pp. 868–874 "The molecular basis of canine pyruvata kinase deficiency".*

* cited by examiner

ANALYSIS OF NUCLEOTIDE POLYMORPHISMS AT A SITE

BACKGROUND OF THE INVENTION

1. Field of the Invention

The present invention relates to methods of determining the identity of a polymorphic nucleotide in a target sequence having at least two variants such as a single nucleotide polymorphism, or SNP. The methods of the present invention utilize primers having sequences complementary to the region upstream of the position being analyzed. Extension of primers hybridized to target sites is carried out in the absence of a deoxyribonucleoside triphosphate (dNTP) or ribonucleoside triphosphate (rNTP) complementary to one of the polymorphic nucleotides. Differences in length between the primers and any extension products reveal the identity of the nucleotide present at the polymorphic site.

2. Background of the Invention

DNA polymorphism can be due to differences in sequence or in length of a genomic region. Approximately 80% of human DNA polymorphisms are sequence polymorphisms, while only about 20% are length polymorphisms. About 90% of sequence polymorphisms are single nucleotide polymorphisms (SNPs). SNPs are genetic variations that arise from differences in the identity of a single nucleotide in a nucleic acid sequence, giving rise to two variants (sometimes called alleles) of that site. Sites having three polymorphic nucleotides have also been detected. SNPs appear to be the most widely distributed genetic markers in the human genome, occurring approximately every kilobase. Since SNPs represent the most common type of DNA sequence variation, the ability to discriminate between variants of these genetic markers is a very important tool in genetic research.

Many inherited diseases are the result of single point mutations at SNP sites. In some cases, the single point mutation causing nucleotide substitution in a protein-encoding gene is sufficient to actually cause the disease, as in sickle cell anemia and hemophilia. For diseases influenced by a large number of genes, including diabetes, heart disease, various cancers, and certain psychiatric disorders, SNPs are studied as markers to aid scientists in creating detailed maps genetic variation to help find disease-linked genes.

SNP markers can be used to identify genes involved in disease or associated with any detectable phenotype by identifying the variant bases of one or more SNPs that correlate with the presence, absence, or degree of severity of the condition. DNA samples are isolated from individuals with and without the disease, and the identity of the polymorphic bases of one or more SNPs from each population are determined. The variants having a statistical association with the disease or phenotype are identified. Thereafter, samples may be taken from individuals and the variant bases of one or more SNPs associated with a disease or phenotype can be identified to determine whether the individuals are likely to develop a particular disease or phenotype, or whether they already suffer from a particular disease or possess a particular phenotype. Mapping SNP markers associated with a disease or phenotype to their chromosomal locations can identify the genes in which they occur, or indicate nearby genes having a role in the development or severity of the disease. By developing a high-density SNP map of the human genome, scientists hope to be able to pinpoint the genetic origins of diseases, the genetic differences that predispose some individuals to disease and underlie variations in individual responses to treatment and, potentially, to predict the most appropriate drugs to treat disease in individuals of a given genetic makeup.

Both the high frequency and wide distribution of SNPs in the human genome makes them a valuable source of biallelic markers for identity testing, genome mapping, and medical diagnostics. SNPs are densely spaced in the human genome, with an estimated number of more than $10^7$ sites scattered along the $3 \times 10^9$ base pairs of the human genome. Because SNPs occur at a greater frequency and with more uniform distribution than other classes of polymorphisms such as variable number of tandem repeat (VNTR) polymorphisms or restriction fragment length polymorphisms (RFLPs), there is a greater probability that SNP markers will be found in close proximity to a genetic locus of interest. SNPs are also preferred as markers because they are mutationally more stable than VNTRs, which have a high mutation rate. In addition, genome analysis using VNTRs and RFLPs is highly dependent on the method used to detect the polymorphism, while new SNPs can easily be detected by sequencing—either random sequencing to detect new SNPs or targeted sequencing to analyze known SNPs.

The different forms of a characterized SNP are easy to distinguish and can therefore be used on a routine basis for genetic typing based on polymorphisms within and between individuals. SNPs correspond to a locus where the sequence differs by a single nucleotide and has only two alleles, making SNPs suitable for highly parallel detection and automated scoring. These features offer the possibility of developing rapid, high-throughput genotyping using SNP analysis.

At present, SNPs can be characterized using any of a variety of methods. These methods include direct or indirect sequencing of the site, oligonucleotide ligation assays (OLAs), ligase/polymerase analysis, use of allele-specific hybridization probes, use of dideoxyribonucleoside triphosphates (ddNTPs) for extension in solution or on solid phase, or use of restriction enzymes to map SNPs. A significant disadvantage of the oligonucleotide ligation assay (OLA) is that this method requires each possible variant of the SNP to be analyzed using a separate set of oligonucleotides for each nucleotide. The main drawback of OLA is that ligation is not a highly discriminating process, such that non-specific signals can occur with an unacceptably high frequency. Techniques such as sequencing, ligase/polymerase analysis, or restriction enzyme mapping are laborious, time-consuming, and often quite expensive for large-scale analysis. Methods such as extension in solution or on solid phase, or ligase/polymerase analysis, rely on incorporation of expensive ddNTPs or labeled dNTPs between bases at a polymorphic site. Since the signal is proportional to the number of ddNTPs or labeled dNTPs incorporated, these methods are often not sensitive enough to be used for routine analysis. For extension on solid phase, primers must first be immobilized to a solid support. Use of a solid support often interferes with hybridization of a primer to the target sequence.

A rapid, accurate, and cost-effective method is needed to meet demands for automated high-throughput analysis of SNPs.

SUMMARY OF THE INVENTION

The present invention provides a simple and effective method for determining the identity of the nucleotide present at a polymorphic site.

The invention involves detection of reaction products of a primer that hybridizes upstream of the polymorphic site. DNA polymerase or RNA polymerase is used to extend the primer in the absence of a dNTP or rNTP complementary to one of the variants at the polymorphic site, for example a SNP.

In detail, the invention provides a method for determining the identity of a nucleotide at a polymorphic site, said method comprising the following steps:

1) Oligonucleotide hybridization: Oligonucleotides having a nucleotide sequence complementary to that of a target molecule known to contain a SNP are hybridized in a manner such that the 3' terminus of the hybridized oligonucleotide is upstream of the preselected site.

2) Polymerase extension: The hybridized primer is incubated with DNA or RNA polymerase and one or more dNTPs or rNTPs, under conditions sufficient to permit template-dependent polymerase incorporation of the dNTP or rNTP to the 3' terminus of the hybridized oligonucleotide. Extension reactions are performed in the absence of a dNTP or rNTP complementary to one of the variants. Extension of the primer to the polymorphic position depends upon whether the reaction mixture contains the dNTP or rNTP complementary to the variant present at the preselected site.

3) Analysis: The reaction products are analyzed to determine whether the primer has been extended to the polymorphic position. Because the extension reactions are performed in the absence of a dNTP or rNTP complementary to one of the variants, the reaction product will not include the polymorphic base if the reaction mixture lacks the complementary nucleotide. Thus, the length of the reaction product depends on whether extension proceeded to the polymorphic position. Suitable methods for analysis include any convenient means of determining the length of the reaction product, including HPLC, capillary electrophoresis, microfluidics technology, or slab gel elecrophoresis. The primers and extension products may be detected using well known methods, including use of intercalators, DNA-binding dyes, or UV light.

DETAILED DESCRIPTION OF THE PREFERRED EMBODIMENT

Figure 1:
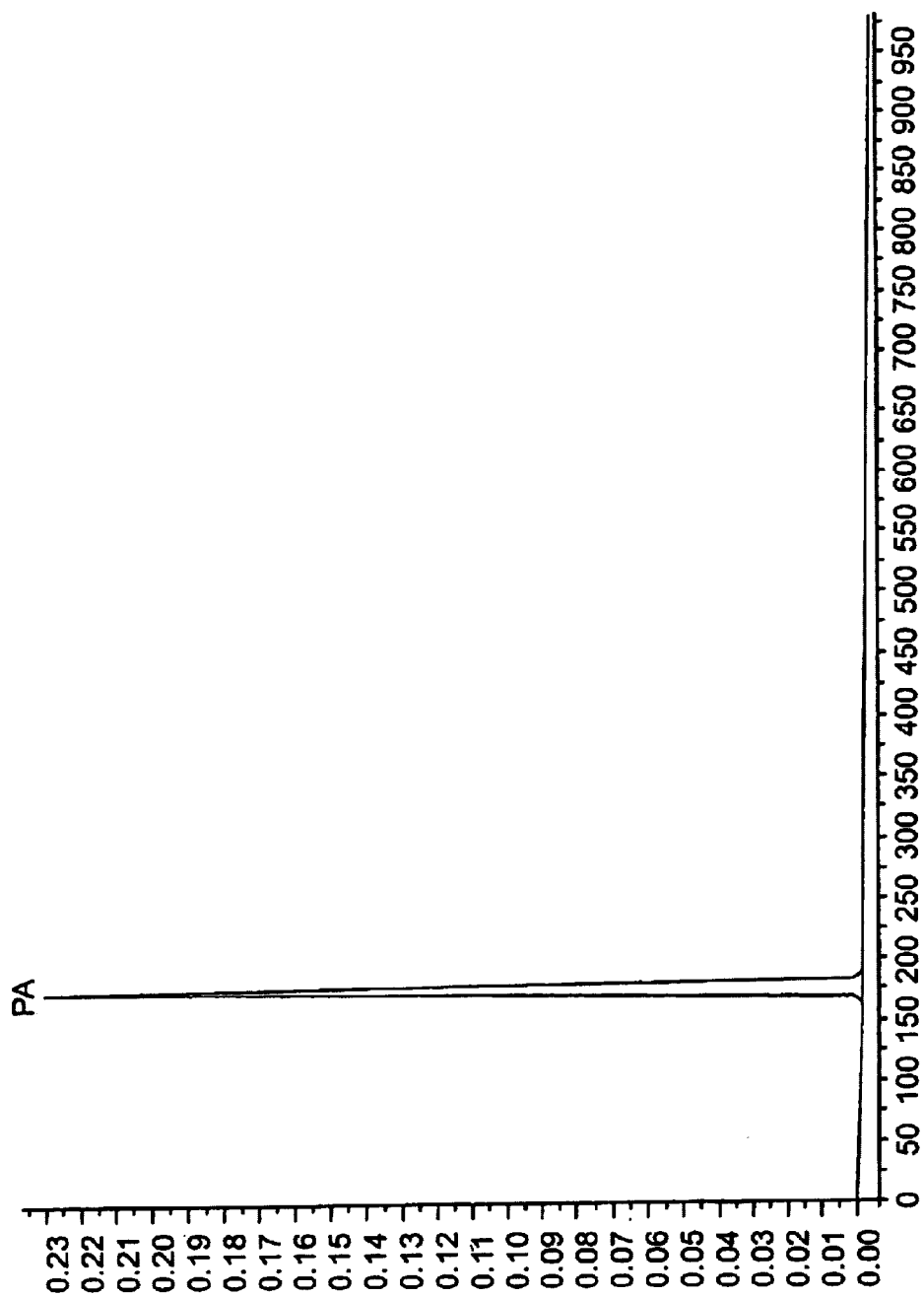
FIG. 1 shows an electropherogram of primer A before the primer extension reaction.

The invention provides a technique for determining the identity of a nucleotide at a polymorphic site having at least two variants by performing one or more primer extension reactions and detecting reaction products. The variants at the polymorphic site may be associated with a detectable trait such as a disease. The first step encompasses obtaining a DNA sample suitable for use in extension reactions. Techniques for DNA isolation from any organism are well known and are routine practice for one skilled in the art.

In one embodiment, a primer is hybridized to a target sequence such that its 3' end is upstream of a polymorphic site having two variants, an extension mixture lacking a dNTP or rNTP complementary to one of the variants is added, and a primer extension reaction is carried out with DNA polymerase or RNA polymerase. The primer may hybridize such that its 3' end is about 1, 2, 3, 4, 5, 10, 15, 20, or more than 20 nucleotides upstream of the polymorphic site. However, it will be appreciated that the primer may hybridize at any location consistent with its intended use. Two parallel reactions are preformed, each lacking one of the dNTPs or rNTPs complementary to one variant. As an illustrative example, a primer hybridizes with its terminus upstream of a target sequence containing a SNP in which one variant of the polymorphic base is A and the other variant of the polymorphic base is T. The sequence between the 3' terminus of the primer and the polymorphic site consists of CGGC; thus, the sequence downstream of the primer for the A variant would be CGGCA, and the sequence downstream of the primer for the T variant would be CGGCT. If the primer extension reaction were carried out in the presence of dCTP, dGTP, and dATP, the primer would be extended by 5 nucleotides or more in reactions performed on DNA samples containing the T variant, and by only 4 nucleotides in reactions performed on DNA samples containing the A variant. In the presence of dCTP, dGTP, and dTTP, the primer would be extended by only 4 nucleotides for the T variant, and by 5 nucleotides or more for the A variant.

In preferred embodiments of the invention, the primers hybridize to the target sequence such that their 3' ends are immediately adjacent to the polymorphic site, and the reaction mixture contains a single dNTP or rNTP complementary to one of the variants, such that the 3'-terminus of a hybridized oligonucleotide is extended by a single nucleotide if the reaction mixture contains a dNTP or rNTP complementary to the polymorphic base in the sample. If the reaction mixture does not include a dNTP or rNTP complementary to the polymorphic base in the sample, the primer will not be extended. In some embodiments, when the target molecule has a homosequence such that the nucleotides following the polymorphic site are the same as the nucleotide at the polymorphic site, the hybridized oligonucleotide is extended by several nucleotides.

The invention encompasses embodiments wherein, after a DNA sample is obtained, an amplification reaction is performed using primers on each side of the polymorphic site in order to dramatically increase the quantity of material containing the polymorphic site being analyzed. The amplification products are then used in the methods of the present invention. Highly preferred amplification methods include the use of polymerase chain reaction (PCR) to amplify DNA sequences, followed by a purification step to remove unincorporated dNTPs. Such a purification step could include the use of column chromatography, for example chromatography over Sephadex media, reaction with exonuclease and alkaline phosphatase, or any other method known to one skilled in the art. In a highly preferred embodiment, after removal of unincorporated dNTPs with exonuclease and alkaline phosphatase, the PCR product containing the polymorphic site is combined with oligonucleotide primer. An extension mixture comprises 20 mM Tris, 10 mM $MgCl_2$, 20 mM NaCl, 500 µM of one dNTP and 1 unit of Sequenase (Taq polymerase). Extension reactions are performed for 10–15 minutes and 25–30 extension cycles.

After the extension reaction is performed, the reaction products are detected to determine whether the primer has been extended to the polymorphic site. Preferably, reaction products are analyzed by HPLC or capillary electrophoresis, using DNA-binding dyes, RNA-binding dyes, or intercalators, e.g., oligogreen, phenanthridines, or acridine, to enhance detection. Preferably, microfluidics technology can be used to analyze the reaction products. In another embodiment, reaction products are analyzed by separation in slab gel or capillary electrophoresis and detected by the use of a DNA-binding dye. Suitable DNA binding dyes include ethidium bromide, DAPI, cyanine dyes, silver stain, indoles and imidazoles. Preferred commercially available dyes include unsymmetrical cyanine dyes available from Molecular Probes, Inc., such as SYBR™ Green I and II, SYBR™ Gold and VISTRA™ Green. In another preferred embodiment, the 5' end of the primer is labeled with a radioactive or nonradioactive tag. For example, the 5' end of the primer may be labelled with $^{32}$P using nucleotide kinase. Reaction products are detected by autoradiography or other suitable methods for detecting radioactively labeled products.

For DNA isolated from diploid organisms such as humans, three different genotypes are possible: homozygous for one allele; homozygous for the other allele, or heterozygous. For analysis of DNA from diploid organisms, a preferred embodiment of the present invention comprises duplication of the hybridization and extension reactions described above, followed by separate or pooled analysis of the reaction products. In one embodiment, the same oligonucleotide primer can be used in separate, parallel reactions where each reaction uses a different deoxyribonucleoside triphosphate. For example, for a C/A polymorphism, the same primer can be used in two reactions, with one reaction mixture containing dGTP and lacking dTTP, and the other reaction containing dTTP and lacking dGTP. Samples from homozygous individuals will contain an extension product including the polymorphic base in only one reaction, whereas samples from heterozygous individuals will contain an extension product including the polymorphic base in both reactions.

In another embodiment, the identity of variant nucleotides at a SNP site in DNA from a diploid organism can be identified by using two oligonucleotide primers of different length. Preferably, only one primer is used in each reaction. The products of separate reactions can be analyzed separately, or pooled and analyzed simultaneously. For example, to analyze a C/A polymorphism, a first extension reaction comprises a 20-base primer hybridizing with its 3' end immediately adjacent to the polymorphic site and reacted in the presence of dGTP and the absence of dTTP. A second reaction comprises a 25-base primer also hybridizing with its 3' end immediately adjacent to the polymorphic site and reacted in the present of dTTP and the absence of dGTP. Separate extensions are performed on aliquots of the same DNA sample, one reaction containing the 20-base primer and dGTP, but lacking dTTP, and the other containing the 25-base primer and dTTP, but lacking dGTP. If the organism from which the DNA was extracted is homozygous for the C variant, then the reaction containing dGTP but lacking dTTP would produce an extension product including the polymorphic base, and the reaction containing dTTP but lacking dGTP would produce no extension product. If the two reactions are pooled for analysis, the pooled reaction products would include 20-base primer and 21-base dGTP extension product from the dGTP reaction, and the 25-base primer from the reaction containing dTTP. If the organism from which the DNA was extracted is homozygous for the A variant, pooled reaction products would include the 25-base primer and 26-base extension product from the reaction containing dTTP, and only the unextended 20-base primer from the reaction containing dGTP. If the organism in question is heterozygous at this SNP, then both the extension reactions would give extension products, producing a pooled mixture of the 20-base primer, 21-base extension product including the G at the polymorphic base, 25-base primer, and 26-base extension product including the T at the polymorphic base.

In another embodiment of the invention, the identity of multiple polymorphic sites in a DNA sample can be determined using multiple primers. Multiple polymorphic sites may serve as markers for a genetic disorder or phenotype, and subtypes of the disorder or phenotype may be distinguishable by determining the nucleotide occurring at each of a plurality of known polymorphic sites. Alternatively, the presence of a particular combination of variants in several SNPs may indicate that an individual is suffering from a particular disease or has a predisposition for a particular disease. In addition, a sample from an individual may be analyzed to determine whether the individual is at risk of developing a plurality of diseases or phenotypes, or currently possesses a plurality of diseases or phenotypes. Thus, the identities of the polymorphic bases of a SNP or combination of SNPs, each of which is associated with a different disease or phenotype, are determined in the sample. In one version of this embodiment, the primer for each site has a distinct length, such that the primer and any extension products can be distinguished from other primers annealing to other sites and their extension products. Preferably, each primer hybridizes with its 3' end immediately upstream of the polymorphic site. In a preferred embodiment, a sample of DNA having multiple polymorphic sites is mixed with primers of differing lengths, where each primer hybridizes upstream of one polymorphic site. The mixture is divided, one dNTP or rNTP is added to each reaction, primer extension is carried out, and the reaction products of each reaction are analyzed. In a highly preferred embodiment, four separate reactions are carried out using either dATP, dTTP, dCTP, or dGTP. Alternatively, each reaction may contain 2 or 3 dNTPs or rNTPs, such that each reaction lacks one dNTP or rNTP. A primer will be extended only if the reaction contains the dNTP or rNTP complementary to the polymorphic nucleotide at the site present in the sample. In this embodiment, a primer will not be extended in reactions containing dNTP or rNTP complementary to the other variants of that site which are not present in the sample, nor will the primer be extended when the reaction contains a dNTP or rNTP complementary to nucleotides that do not occur at that site. The products of each reaction may be analyzed separately or, depending on the particular polymorphic sites being tested, may be pooled for analysis. This invention encompasses embodiments using multiple primers to identify the polymorphic nucleotides at a plurality of sites in DNA isolated from a diploid organism.

In another preferred embodiment, a sample of DNA containing one or more target sequences having a polymorphic site is mixed with primers which hybridize to each of the strands of the of the target sequence such that the 3' ends of the primers are upstream of the polymorphic site. Preferably, the primers have different lengths such that their extension products can be distinguished. Thus, at each polymorphic site, two primers, each of which hybridize to one of the strands containing the polymorphic nucleotide, can be used to identify the variant or variants present in the target DNA. Preferably, one primer hybridizes to the first strand such that its 3' terminus is adjacent to the polymorphic site on the first strand while the second primer hybridizes to the opposite strand, such that its 3' terminus is adjacent to the polymorphic site on the opposite strand. However, as discussed herein, the primers may also hybridize such that their 3' ends are more than one nucleotide upstream of the polymorphic site. If the primers are of differing lengths, a single extension reaction can be carried out to determine the variants present at a polymorphic site in a diploid DNA sample. For example, if a sample has a T/C polymorphic site on the first DNA strand, a first primer having 19 bases hybridizes to the first DNA strand such that its 3' terminus is adjacent to the polymorphic site. If the T variant is present on the first strand, this primer will be extended in the presence of dATP. A second primer having 22 bases hybridizes to the opposite strand, such that its 3' terminus is adjacent to the polymorphic site. If the C variant is present on the first DNA strand, then the opposite DNA strand would contain G in position opposite the first-strand polymorphic site, such that the second primer hybridized to the opposite DNA strand would be extended in the present of dCTP. Thus, a single extension reaction is carried out, where the reaction mixture contains both primers and dATP and dCTP but lacks dTTP and dGTP. Analysis of the reaction products reveals the variant(s) present at the polymorphic site: a sample homozygous for the T variant would produce 20-base long dATP extension products of the 19-base primer that hybridizes to the first DNA strand; a sample homozygous for the C variant would produce 23-base-long dCTP extension products of the second primer that hybridizes to the opposite DNA strand; a DNA sample heterozygous for both variants would produce extension products of both primers. Alternatively, if the primers are the same length, then two separate extension reactions are carried out. The first extension reaction contains one primer and the nucleotide complementary to one of the variants at the polymorphic site but lacks the nucleotide complementary to the other variant, while the second extension reaction contains the other primer and the nucleotide complementary to the other variant but lacks the nucleotide complementary to the first variant. If the sample is homozygous for one of the variants, an extension product will be observed in one of the extension reactions. However, if the sample is heterozygous, extension products will be observed in both extension reactions.

Another preferred embodiment comprises a kit or kits containing materials suitable for practicing the present invention. Such kits may include, but are not limited to, primers which hybridize upstream of known polymorphic sites of interest, reagents for carrying out annealing and primer extension reactions, and materials for purification and detection of primers and reaction products, including materials to enhance detection of reaction products. Kits may contain reagents for amplifying the polymorphic site prior to carrying out primer extension reactions.

It will be appreciated that the present invention can be practiced using isolated RNA, RNA oligonucleotide primers, RNA polymerase, and rNTPs. Proper precautions to avoid degradation of the RNA can be routinely practiced by one of skill in the art, using well-known methods.

Example 1 describes the use of the present invention to identify the variants of a human gene known to be involved in cancer.

EXAMPLE 1

The exon 8 mutation (T to G) of the hMSH2 gene was used as a model for analysis of DNA polymorphism. The hMSH2 gene codes for a DNA mismatch repair protein, and inherited defects in the gene7 have been linked with the development of hereditary non-polyposis colorectal cancer (NHPCC). This gene is located on chromosome 2p and is comprised of sixteen exons. Multiple mutations responsible for NHPCC have been identified and are widely interspersed throughout the gene. (Liu B., R. E. Parsons, S. R. Hamilton, G. M. Petersen, H. T. Lynch, P. Watson, J. Green, A. dela Chapelle, K. W. Kinzler and B. Vogelstein. hMSH2 mutations in hereditary nonpolyposis colorectal cancer kindreds. *Cancer Research* 54: 4590–4594 (1995), the disclosure of which is incorporated herein by reference in its entirety. The sequence of the hMSH2 region containing the exon 8 polymorphic site is provided in the accompanying sequence listing as SEQ ID NO: 1. As indicated in the sequence listing, SEQ ID NO: 1 contains a polymorphic base having two variants, T and G, at position 165. Genomic DNA samples were isolated from individuals having different mutations at the same site in exon 8 of hMSH2. A section of exon 8 including the polymorphic site was amplified from each genomic sample using the sense direction primer: 5' TGTAAAACGACGGCCAGT (SEQ ID NO: 2) and the antisense primer: 5' CAGGAAACAGCTATGACC (SEQ ID NO: 3). Exon 8 was amplified in 20 $\mu$l reaction volume using 600 nM each of the respective sense and antisense PCR primers, 20 ng of genomic DNA, 200 $\mu$M of each dNTP, 1 unit (U) Taq Gold, 10 mM Tris-HCL pH 8.3, 50 mM KCl. The first cycle was carried out at 94° C. for 2 minutes, followed by thirty cycles of 94° for 30 seconds, 60° C. for 1 minute, and 72° C. for 30 seconds.

The PCR product containing the polymorphic site was 234 bases in length, covering the coding region of exon 8 of hMSH2 and the intron region immediately flanking it. Unincorporated bases were removed using exonuclease and shrimp alkaline phosphatase in a reaction mixture containing 5 $\mu$l of the PCR mixture, 2 U shrimp alkaline phosphatase and 2 U exonuclease I, in a 10 $\mu$l final volume buffered to pH 8.0. The mixture was incubated at 37° C. for 30 minutes, and then at 94° C. for 10 minutes to deactivate the enzymes.

The identity of the polymorphic nucleotide at the exon 8 site was established using two primers of different lengths which hybridize with their 3' ends immediately upstream of the polymorphic base: Primer A, a 15-base primer, was used to detect for the G-mutation in an extension mixture containing only dCTP; Primer B, an 18-base primer, was used to detect the T-mutation in an extension mixture containing only dATP.

Primer A: 5' ACCTGATCCATATCT (SEQ ID NO: 4)

Primer B: 5' ATACCTGATCCATATCT (SEQ ID NO: 5)

The extension reaction mixture contained 10 $\mu$l purified PCR product containing the exon 8 polymorphic site, 10 pmol of primer, 2 $\mu$M dCTP or dATP, 1 U thermosequenase, in a 20 $\mu$l reaction volume containing 20 mM Tris-HCL pH 9.5 and 4 mM $MgCl_2$. The mixture was denatured for 1 cycle at 95° C. for 4 minutes, followed by 20 cycles of primer extension (55° C. for 15 seconds, 72° C. for 4–10 seconds; 94° C. for 10 seconds). The reaction was ethanol-precipitated or purfied over Sephadex G-50. Purified reaction products were diluted in 10–20 $\mu$l water or 80% formamide, and SYBR Green II (cyamide dye, Molecular Probes, Inc.) was added to a final concentration of between 1:1000 to 1:16000, preferably 1:5000. Reaction products containing the intercalator were injected electrokinetically for 1 minute at 3.5 kV, and run at 7–9 kV at room temperature, using a 62 cm capillary tube (coated, 200 $\mu$m O.D./75 $\mu$m I.D., Polymicro Technologies, Phoenix, Ariz., U.S.A.) A 50 mW, 488 nm argon ion ($Ar^+$) laser (Melles Griot, Carlsbad, U.S.A.) was used as the excitation source, with the detection window located 40 cm from the injection site. Sieving polymers used for separation by capillary electrophoresis (CE) include linear polyacrylamide or various cellulose derivatives. Other suitable separation media may also be used for CE separation.

Figure 2:
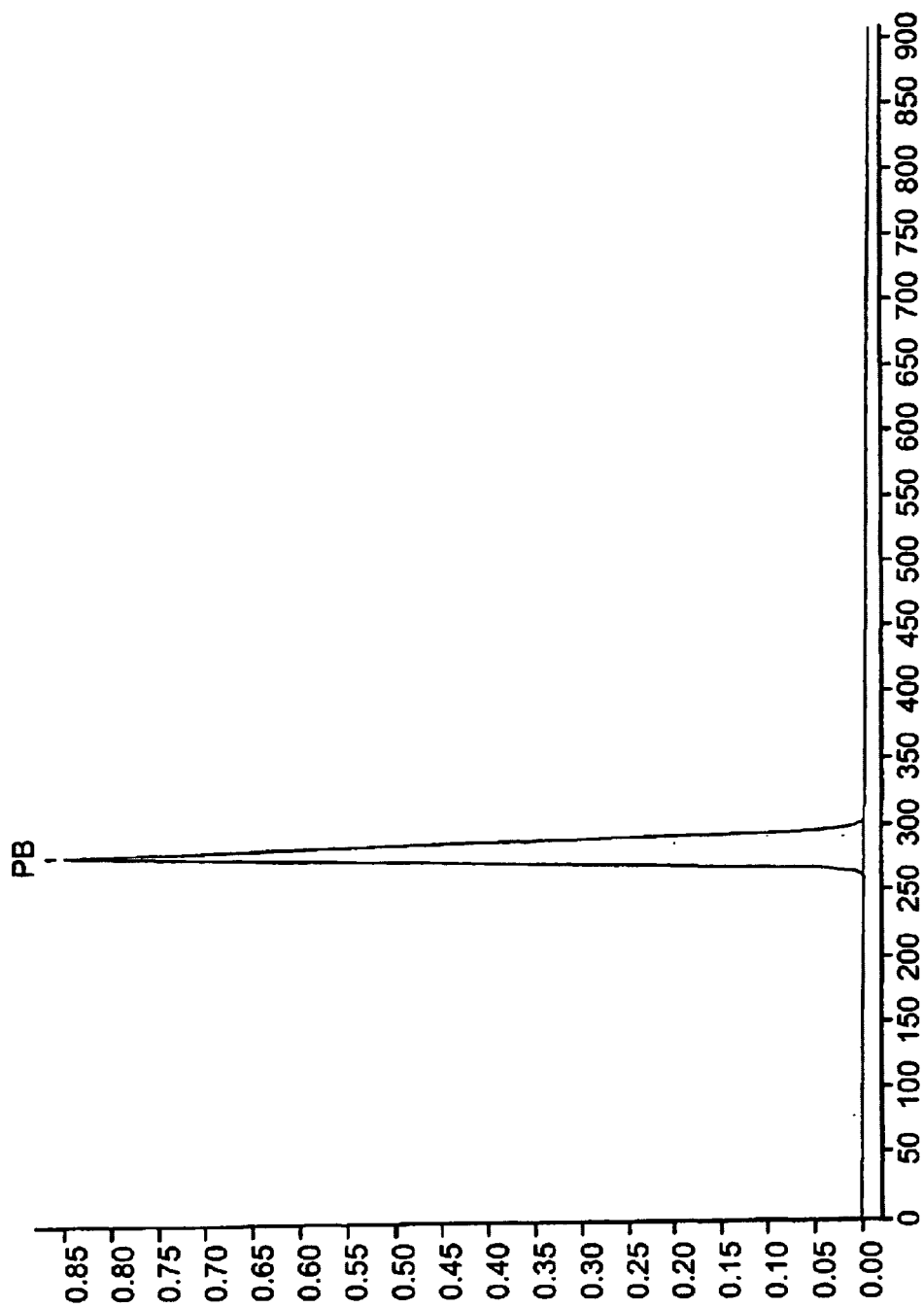
FIG. 2 shows an electropherogram of primer B before the primer extension reaction.

FIG. 1 shows an electropherogram of the 15-base oligonucleotide primer A before carrying out an extension reaction. FIG. 2 shows an electropherogram of the 18-base oligonucleotide primer B before carrying out an extension reaction.

Figure 3:
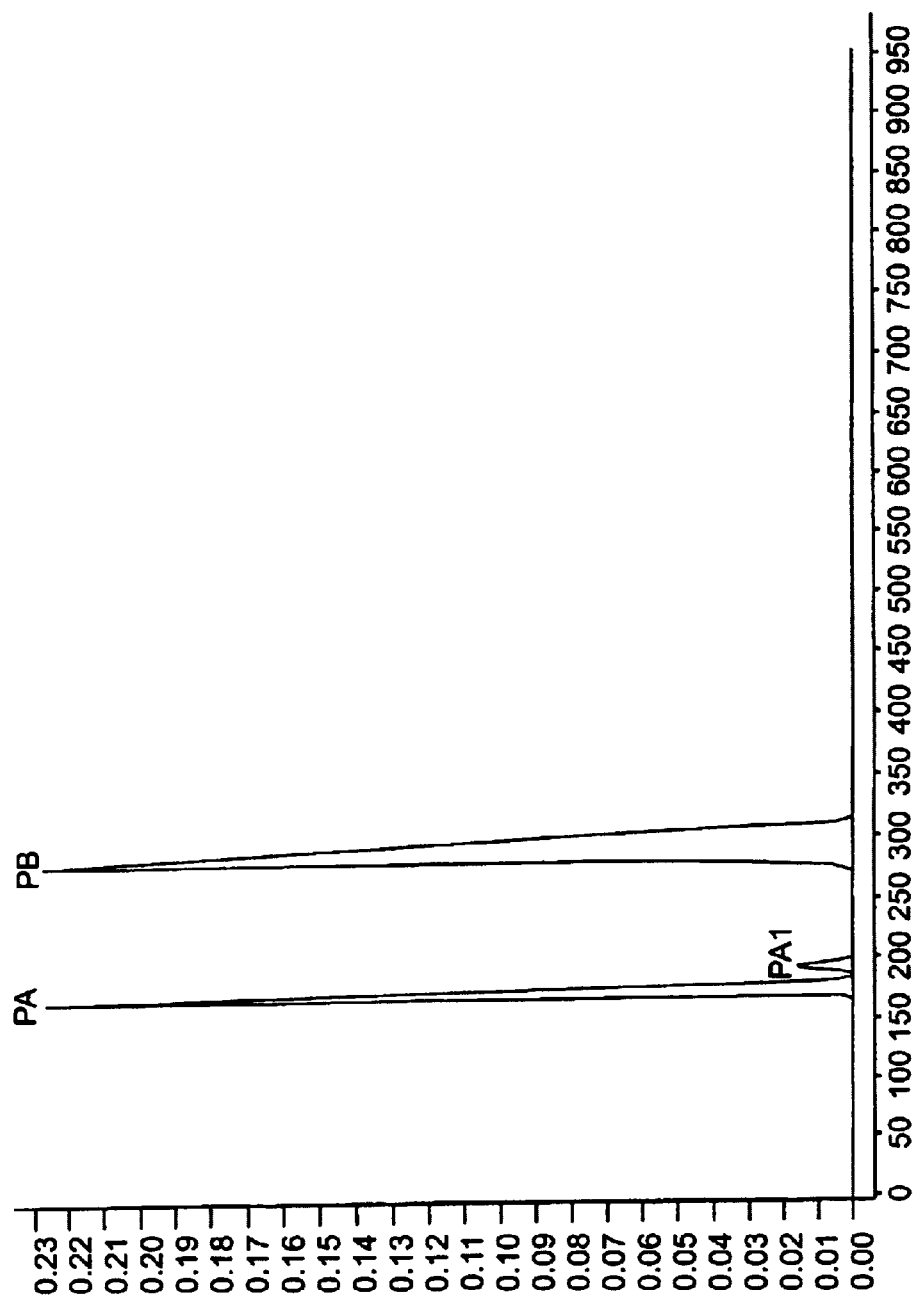
FIG. 3 shows an electropherogram of reaction products from DNA homozygous for the G mutation of exon 8 of hMSH2. The first peak corresponds to primer A (PA), the second peak corresponds to its extension product (PA1), and the third peak corresponds to primer B (PB).

FIG. 3 shows the pooled reaction products obtained using DNA from an individual homogyzous for the G mutation of exon 8 of hMSH2. One extension reaction was carried out using Primer A (SEQ ID NO: 4) and only dCTP, while a parallel extension reaction was carried out using Primer B (SEQ ID NO: 5) and only dATP. After the reactions were completed, they were pooled and their products analyzed by capillary electrophoresis as described above. The products included the 15-base primer A (PA) and its 16-base extension product, PA 1. Primer B was not extended because it was used in an extension reaction lacking the nucleotide complementary to the G variant of the polymorphic site present in the sample.

Figure 4:
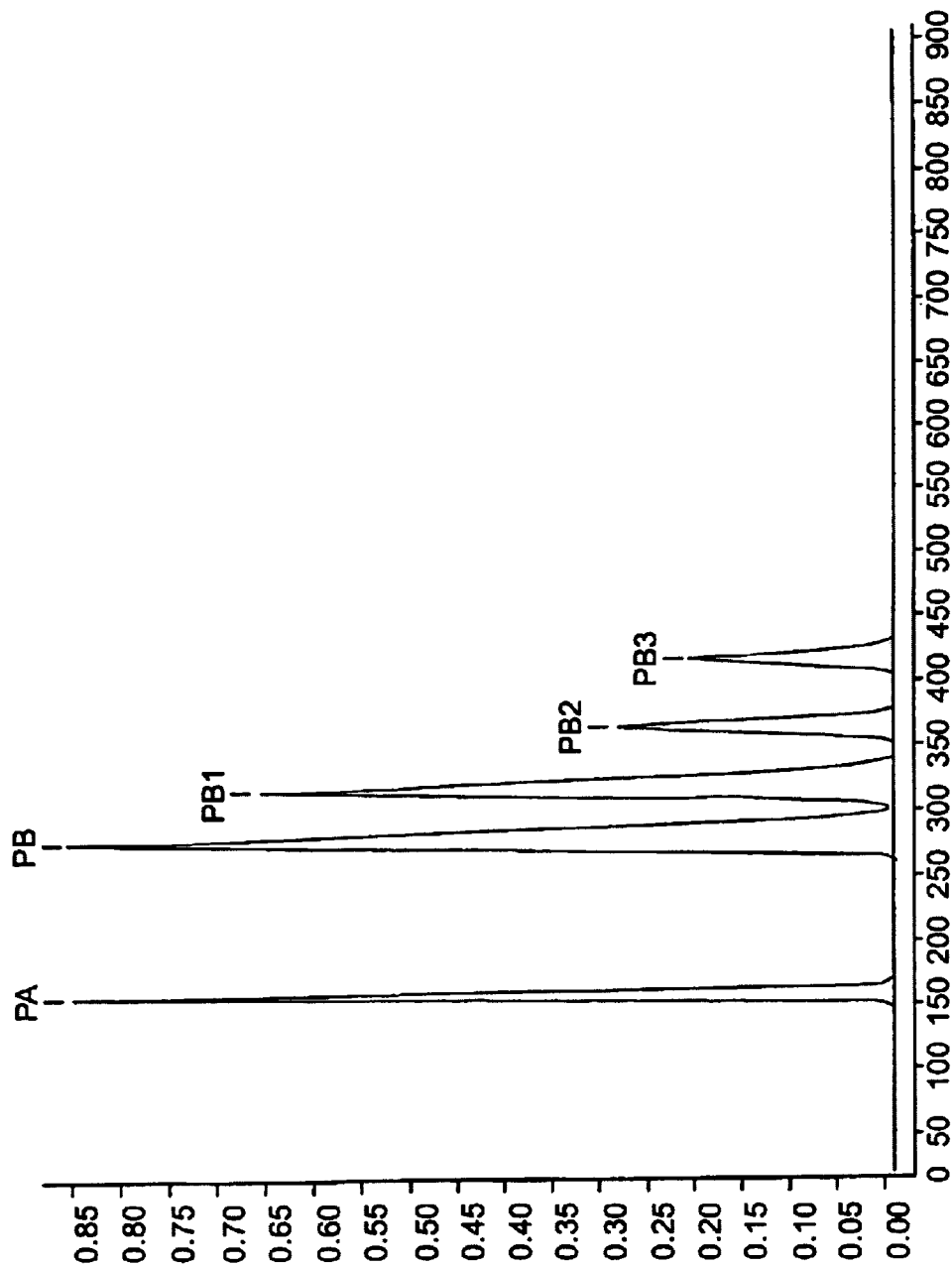
FIG. 4 shows an electropherogram of reaction products from DNA homozygous for the T mutation of exon 8 of the hMSH2 gene. The first peak corresponds to primer A (PA), and the second group of peaks corresponds to primer B (PB) and its extension products (PB1, PB2, PB3).

FIG. 4 shows the pooled reaction products obtained using DNA from an individual homogyzous for the T mutation of exon 8 of hMSH2. One extension reaction was carried out using Primer A (SEQ ID NO: 4) and only dCTP, while a parallel extension reaction was carried out using Primer B (SEQ ID NO: 5) and only dATP. After the reactions were completed, they were pooled and their products analyzed by capillary electrophoresis as described above. Primer A (PA) was not extended in the reaction lacking the nucleotide complementary to the T variant of the polymorphic site present in the sample. The reaction containing Primer B and dATP gave multiple extension products: unextended 18-base primer B (PB); the 19-base extension product formed by incorporating a nucleotide complementary to the T variant of the polymorphic site at position 165; and additional extension products resulting from the homosequence of two Ts at positions 164 and 163, immediately downstream of the polymorphic nucleotide, giving rise to 20-base (PB2) and 21-base (PB3) extension products.

Figure 5:
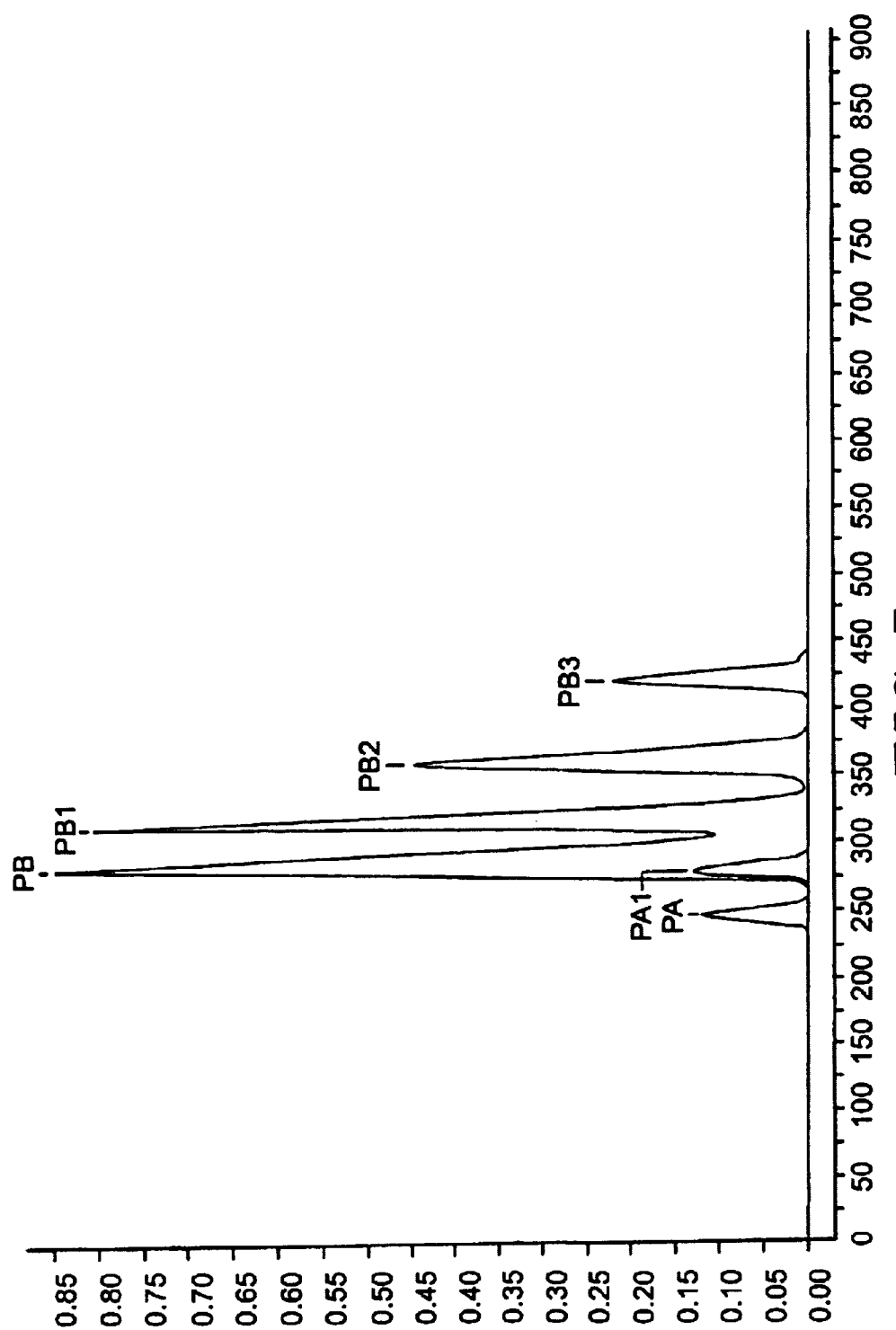
FIG. 5 shows an electropherogram of reactions from DNA heterozygous for both the G and T mutations of exon 8 of the hMSH2 gene.

FIG. 5 shows the pooled reaction products obtained using DNA from an individual heterozygous for the variants of exon 8 of hMSH2. One extension reaction was carried out using Primer A (SEQ ID NO: 4) and dCTP, and a parallel extension reaction was carried out using Primer B (SEQ ID NO: 5) and DATP. After the reactions were completed, they were pooled and their products analyzed by capillary electrophoresis as described above. One copy of the hMSH2 target sequence present in the sample had the G variant, such that the reaction containing Primer A and dCTP produced extension product PA1 from Primer A (PA). The other copy of the hMSH2 target sequence present in the sample had the T variant, such that the reaction containing Primer B and dATP produced the same extension products seen in FIG. 4, namely Primer B (PB), PB1, PB2, and PB3.

Example 2 describes the use of the present invention with radioactively labeled VA primer to identify the variants of a PCR product.

EXAMPLE 2

The following PCR product was used as a model system. The nucleotide indicated in bold type is located at the polymorphic site. In this sample, the A variant is present on the strand to be analyzed.

5' GACGAATTCTAATACGACTCACTAT-AGGGTAAGGCCAAACGTTTAACT 3' (SEQ ID NO: 6)

5' AGTTAAACGTTTCGCCTTACCCTATAGT-GAGTCGTATTAGAATTCGTC 3' (SEQ ID NO: 7)

PRIMER: 5' TAATACGACTCACTATAGGG 3' (SEQ ID NO: 8)

Reaction conditions were as described in Example 1, except that the primer was radioactively labelled with γ-$^{32}$ATP. After the reaction was complete, the reaction products were separated on a 20% polyacrylamide slab gel and products were detected by autoradiography of the gel. The lanes of the gel contained the following: Control Lane with labeled primer only; Lane A, reaction products with dATP added, Lane T, reaction products with dTTP added; Lane C, reaction products with dCTP added. The samples in Lanes A (DATP added) and C (dCTP added) migrate the same distance as the 20-base primer control (Control Lane), indicating that the primer was not extended in those reactions. However, the reaction products in Lane T (dTTP to reaction) shows an extension product. The primer was extended by addition of a single base (here, dTTP) to make a 21-base product. The small amount of radioactivity seen in the 20-base position indicates that the reaction did not extend all of the radioactively labeled 20-base primer present.

What is claimed is:

1. A method for determining the identity of a polymorphic nucleotide in a target sequence having at least two known variant nucleotides at a site, comprising:
  performing a primer extension reaction with the target sequence using an extension reaction mixture comprising:
    a primer that specifically hybridizes to the target sequence such that there is a one or more nucleotide gap between the 3' terminus of the primer and the variant nucleotide of the polymorphic site of the target sequence, and
    a mixture of deoxyribonucleoside triphosphates (dNTPs) or ribonucleoside triphosphates (rNTPs), where the mixture of dNTPs or rNTPs provide for at least one nucleotide extension of the primer when hybridized to a target sequence having either of the two variant nucleotides at the polymorphic site, wherein the mixture excludes a dNTP or rNTP complementary to one of said variant nucleotides of the polymorphic site, and wherein the dNTPs or rNTPs in the mixture are not detectably labeled or modified, and wherein the extension reaction is performed in the absence of a dideoxynucleoside triphosphate (ddNTP); and
  analyzing primer extension products of said extension reaction;
  wherein the length of the primer extension products is indicative of the identity of the variant nucleotides at the polymorphic site.

2. The method of claim 1, wherein the primer hybridizes to the target sequence such that there is a gap of at least two nucleotides between the 3' terminus of the primer and the variant nucleotide of the polymorphic site of the target sequence.

3. The method of claim 1, wherein said analyzing comprises determining the length of said reaction products.

4. The method of claim 1, wherein said analyzing comprises performing a technique selected from the group consisting of chromatography, capillary electrophoresis, microfluidic analysis, and slab gel electophoresis.

5. The method of claim 1, wherein said analyzing primer comprises performing high performance liquid chromatography.

6. The method of claim 1, wherein said analyzing comprises performing capillary electrophoresis.

7. The method of claim 1, wherein said analyzing primer extension products comprises determining the identity of a nucleotide incorporated in a reaction product.

8. The method of claim 1, wherein said analyzing comprises use of an intercalating agent.

9. The method of claim 8, wherein the intercalating agent is ethidium bromide.

10. Tho method of claim 8, wherein the intercalating agent is an unsymmetrical cyanin dye.

11. The method of claim 1, wherein said analyzing comprises use of slab electrophoresis and ultraviolet light.

12. The method of claim 1, wherein the reaction products are detected using slab electrophoresis and a DNA-binding dye.

13. The method of claim 1, wherein the target sequence comprises a biallelic marker associated with genetic disorders.

14. The method of claim 1, wherein the target sequence is present in a sample obtained from a diploid organism.

15. A method for screening a DNA sample for a plurality of target sequences having at least two known variants, comprising:
  contacting a sample comprising a plurality of known target sequences with an extension reaction mixture to produce primer extension reaction products, the extension reaction mixture comprising
    a primer that specifically hybridizes to a target sequence of interest such that there is one or more nucleotide gap between the 3' terminus of the primer and one the variant nucleotide of the polymorphic site of the target sequence, and
    a mixture of deoxyribonucleoside triphosphates (dNTPs) or ribonucleoside triphosphates (rNTPs), where the dNTPs or rNTPs in the mixture provide for at least one nucleotide extension of the primer when hybridized to a target sequence having either of the two variant nucleotides, the mixture excluding a dideoxynucleoside triphosphate (ddNTP) and further excluding a dNTP or rNTP complementary to one of said variant nucleotides of the SNP, wherein the dNTPs or rNTPs in the mixture are not detectably labeled or modified; and
  analyzing the primer extension products;
  wherein the length of the primer extension products is indicative of the identity of the variant nucleotides at the polymorphic site.

16. The method of claim 15, wherein the target sequence is associated with genetic disorders.

17. The method of claim 15, wherein the sample is from a diploid organism.

18. The method of claim 15, wherein the extension reaction mixture comprises at least two different primers, which primers specifically hybridize to a different target sequences, wherein each primer is of a length or sequence such that extension products of the different primers can be distinguished one from another.

19. The method of claim 18, wherein the different primers are of different lengths.

* * * * *

UNITED STATES PATENT AND TRADEMARK OFFICE
CERTIFICATE OF CORRECTION

PATENT NO. : 6,762,018 B1
DATED : July 13, 2004
INVENTOR(S) : Irena N. Merenkova It is certified that error appears in the above-identified patent and that said Letters Patent is hereby corrected as shown below:

Column 13,
Line 24, the word "provide" should be -- provides --.
Line 52, the word "primer" after the word "analyzing" and before the word "comprises" should be removed.

Signed and Sealed this

Sixteenth Day of November, 2004

JON W. DUDAS
*Director of the United States Patent and Trademark Office*

SEQUENCE LISTING

<160> NUMBER OF SEQ ID NOS: 8

<210> SEQ ID NO 1
<211> LENGTH: 304
<212> TYPE: DNA
<213> ORGANISM: Homo sapiens

<400> SEQUENCE: 1

| | | | | | |
|---|---|---|---|---|---|
| aaaattttat | gatttgtatt | ctgtaaaatg | agatcttttt | atttgtttgt | tttactactt | 60 |
| tcttttagga | aaacaccaga | aattattgtt | ggcagttttt | gtgactcctc | ttactgatct | 120 |
| tcgttctgac | ttctccaagt | ttcaggaaat | gatagaaaca | acttkagata | tggatcaggt | 180 |
| atgcaatata | cttttttaatt | taagcagtag | ttatttttaa | aaagcaaagg | ccactttaag | 240 |

-continued

```
aaagtttgta gattttttt tttagtatct aaatgtagca cctttgtgga cagtggatgt    300
aata                                                                304

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide

<400> SEQUENCE: 2
tgtaaaacga cggccagt                                                 18

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide

<400> SEQUENCE: 3
caggaaacag ctatgacc                                                 18

<210> SEQ ID NO 4
<211> LENGTH: 15
<212> TYPE: DNA
<213> ORGANISM: Artificial Sequence
<220> FEATURE:
<223> OTHER INFORMATION: Oligonucleotide

<400> SEQUENCE: 4
acctgatcca tatct                                                    15

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide

<400> SEQUENCE: 5
catacctgat ccatatct                                                 18

<210> SEQ ID NO 6
<211> LENGTH: 48
<212> TYPE: DNA
<213> ORGANISM: Homo sapiens

<400> SEQUENCE: 6
gacgaattct aatacgactc actatagggt aaggccaaac gtttaact                48

<210> SEQ ID NO 7
<211> LENGTH: 48
<212> TYPE: DNA
<213> ORGANISM: Homo sapiens

<400> SEQUENCE: 7
agttaaacgt ttcgccttac cctatagtga gtcgtattag aattcgtc                48

<210> SEQ ID NO 8
<211> LENGTH: 20
<212> TYPE: DNA
<213> ORGANISM: Artificial Sequence
<220> FEATURE:
```

-continued

```
<223> OTHER INFORMATION: Oligonucleotide

<400> SEQUENCE: 8
taatacgact cactataggg                                                      20
```